United States Patent [19]

Gordon

[11] 4,341,208

[45] Jul. 27, 1982

[54] MOISTURE-RETENTIVE COVERING FOR OINTMENT APPLICATION

[75] Inventor: Marvin Gordon, East Windsor, N.J.

[73] Assignee: Whitman Medical Corporation, Clark, N.J.

[21] Appl. No.: 168,723

[22] Filed: Jul. 14, 1980

[51] Int. Cl.³ .............................................. A61L 15/00
[52] U.S. Cl. .................................... 128/156; 128/268
[58] Field of Search ............................. 128/155–156, 128/171, 260, 261, 268; 206/570, 440, 441, 828; 424/28, 349

[56] References Cited

U.S. PATENT DOCUMENTS

| | | | |
|---|---|---|---|
| 2,273,873 | 2/1942 | Klein | 128/156 |
| 2,561,071 | 7/1951 | Prisk | 128/260 |
| 3,797,494 | 3/1974 | Zaffaroni | 128/268 |
| 3,972,995 | 8/1976 | Tsuk et al. | 128/268 |
| 3,996,934 | 12/1976 | Zaffaroni | 128/268 |

Primary Examiner—C. Fred Rosenbaum
Attorney, Agent, or Firm—Holman & Stern

[57] ABSTRACT

A moisture-retentive covering for ointment, such as nitroglycerin, applied for percutaneous absorption includes a flexible frame member having first and second surfaces with adhesive material thereon. A sheet of moisture-impervious material is secured to the first surface of the frame member and entirely covers the first surface and the area prescribed within the frame. A removable backing is secured to the second surface. A tab extends from the sheet of moisture-impervious material to permit the covering to be gripped while the removable backing is peeled away.

6 Claims, 6 Drawing Figures

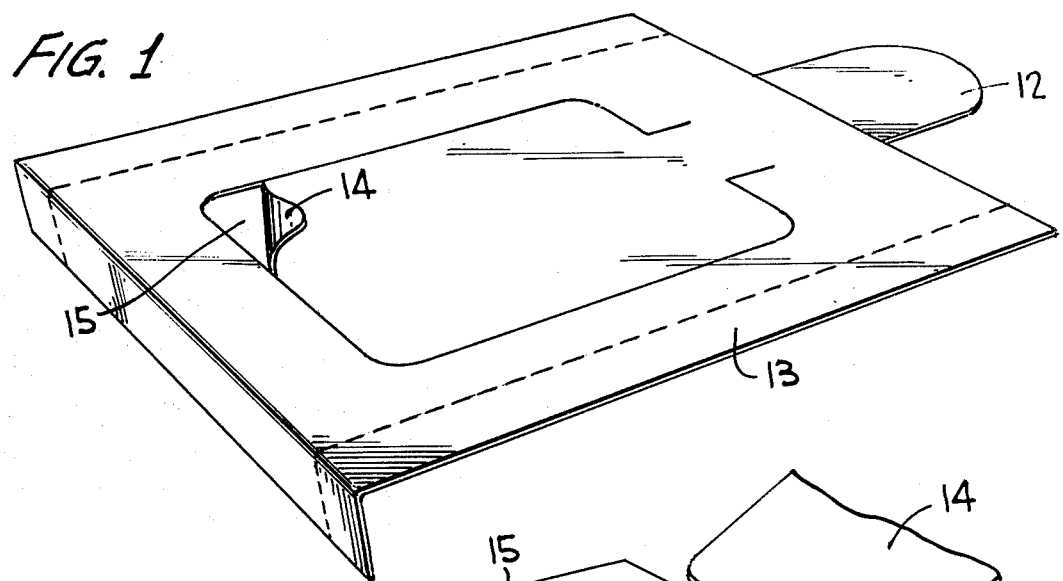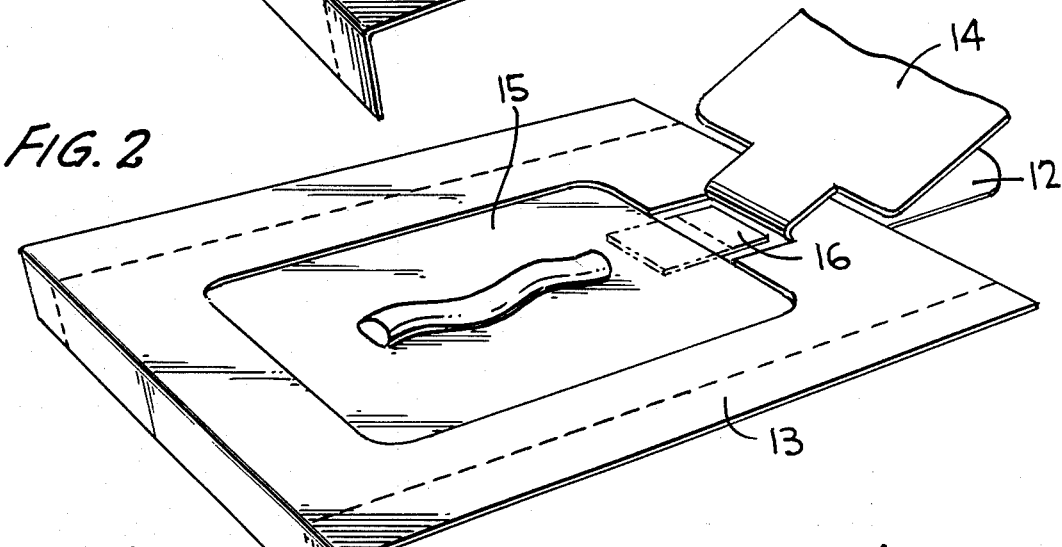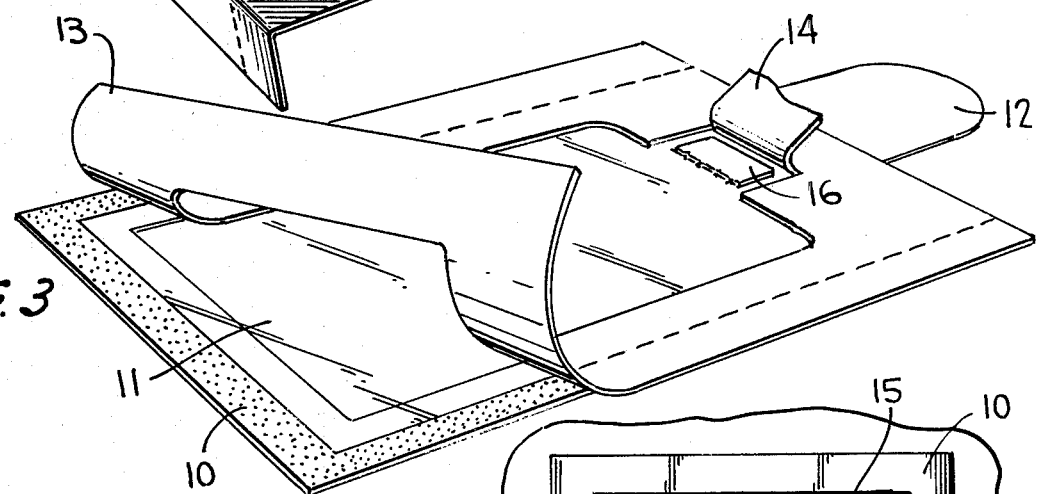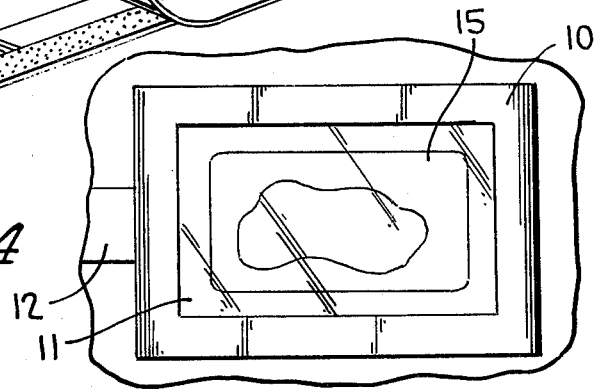

MOISTURE-RETENTIVE COVERING FOR OINTMENT APPLICATION

TECHNICAL FIELD

The present invention relates to medical ointment and salve application. More particularly, the present invention relates to a covering for the situs of ointment or salve application which simplifies application and renders percutaneous absorption of the ointment more efficient. Although the present invention is described in relation to application of nitroglycerin percutaneously, it is to be understood that the scope of the invention incorporates application of other percutaneously administered ointments or salves.

BACKGROUND OF THE INVENTION

Nitroglycerin has long been recognized as a vasodilator having no significant toxic or other side effects. As a consequence, nitroglycerin has served extremely well in the treatment of angina pectoris. It has also been recognized that nitroglycerin is useful in treating such peripheral circulatory disorders as Raynaud's disease. Recent studies suggest that nitroglycerin ointment may be of value in treating patients having acute myocardinal infarction and congestive heart failure.

Nitroglycerin (glyceryl trinitrate) acts to relax vascular smooth muscle, thereby having a marked effect on the cardio-vascular system. In essence, the nitroglycerin decreases peripheral resistance to thereby produce a decrease in systolic blood pressure; it is also thought to dilate coronary blood vessels to thereby increase blood flow to the myocardium.

One of the disadvantages of nitroglycerin resides in the fact that in any form its effective life is very short. Once it reaches the portal circulation, it is rapidly cleared from the blood by the liver. Orally administered nitroglycerin is absorbed from the gastrointestinal tract and is degraded before it reaches the circulation system. Sublingually administered nitroglycerin is released directly into the circulatory system under the tongue, thereby avoiding destruction in the gastrointestinal tract and portal circulation.

The duration of nitroglycerin effect is related to the rate at which it can be absorbed into the circulation system. In sublingual administration, the vasodilating effects last 15 to 30 minutes. The development of nitroglycerin in ointment form has made it possible to sustain its effect for up to five hours. It is administration of the nitroglycerin in ointment form with which this invention is concerned.

Several factors influence percutaneous absorption of substances such as nitroglycerin ointment, primarily because the network of glands and vasculature in the skin is so complex. The stratum corneum, the outermost layer of the epidermis and principal barrier of the skin, plays an important role in absorption of substances applied to the skin. The passage of substances from the skin takes place primarily through hair follicles and sweat ducts in this skin layer. The main driving force through absorption of the skin is a concentration gradient. However, lipid material around and between the cells of the stratum corneum and within the openings of the apendages of the skin also play a major role in absorption. These lipids, along with water present in and around the cells, determine the kind of substances that will defuse easily across the skin. Increased hydration of the stratum corneum appears to expand the pores or channels in the skin and increases permeability of substances. Therefore, skin moisture affects the percutaneous absorption of nitroglycerin ointment.

While the application of nitroglycerin topically has become an accepted means of obtaining prolonged vasodilation, the actual measuring and applying the ointment has received scant attention. Conventionally, application of nitroglycerin ointment is performed by squeezing a prescribed dose of the ointment from a tube onto a dose measuring application paper. Typically, the dose is one to two inches in length, although some patients require higher dosages. The application paper is then applied, ointment side down, at any convenient, hairless sight on the patients body, usually the anterior chest. The application paper is then taped to the sight by suitable medical tape or the like. Finally, the sight is covered with plastic wrap which is taped to the patient's skin on all sides. Increases in skin temperature and hydration, which, in turn, enhances percutaneous absorption. This multi-step application process requires the nurse or other health care personnel to cut the plastic wrap and individual tape strips in advance and then hold the plastic wrap in position at each individual tape strip applied. This procedure, although seemingly simple in description, is awkward for the nurse and relatively time consuming.

SUMMARY OF THE INVENTION

It is an object of the present invention to simplify the application of ointments, such as nitroglycerin, which are applied topically for percutaneous absorption. More specifically, it is a primary object of the present invention to provide a moisture retentive covering for ointment application which is simple to prepare and use. It is another object of the present invention to provide such a covering which effectively seals the area around and under an ointment applicator while keeping the applicator in place and preventing liquid leakage of the ointment from under the applicator.

In accordance with one aspect of the present invention, a covering for a topically applied salve or ointment comprises a frame, preferably rectangular in shape, of double sided adhesive tape, such as medical tape having adhesive material on both sides. A sheet of moisture impervious material is adhered to one side of the frame, filling the entire area within the outer periphery of the frame. This sheet of material includes a projecting portion, which extends beyond the periphery of the frame, much like a tab. The other side of the frame, prior to use, is covered with a conventional removable backing. In applying the ointment to a portion of a patient's skin, a dose measuring application paper receives the measured ointment dose, as in the prior art, and is applied to the selected area of the body. The removable backing, on the frame of the covering of the present invention, is then peeled off and the covering is placed adhesive side down, over the dose measuring applicator. The tape provides a border seal while the water impervious sheet material seals in moisture and increases skin hydration and temperature.

In one embodiment of the present invention, the dose measuring applicator is provided as part of the moisture retentive covering assembly and the removable backing covers the entire area within the periphery of the frame. A perforated flap or tab forms parts of the removable backing and covers the dose measuring applicator. In use, the tab is folded back and pulled away from the dose measuring applicator so that ointment can be applied to the applicator. Holding the tab of the moisture impervious material, the nurse peals away the entire removable backing and applies the entire assembly, dose measuring applicator and covering, to the desired sight. Alternatively, the dose measuring applicator can be removed along a perforation and applied to the sight prior to removing the overall removable backing from the covering unit.

BRIEF DESCRIPTION OF THE DRAWINGS

The embodiments of the present invention will become more clear when taken in conjunction with the drawings, wherein:

FIG. 1 is a view in perspective of the first embodiment of the present invention fully intact and prior to use;

FIG. 2 is a view in perspective of the covering of FIG. 1 with a perforated tab removed;

FIG. 3 is a view in perspective of the covering of FIG. 1 illustrating how the removable backing is stripped away immediately prior to use;

FIG. 4 is a plan view showing the covering of FIG. 1 applied to the body of a patient;

DESCRIPTION OF THE PREFERRED EMBODIMENTS

Figure 5:
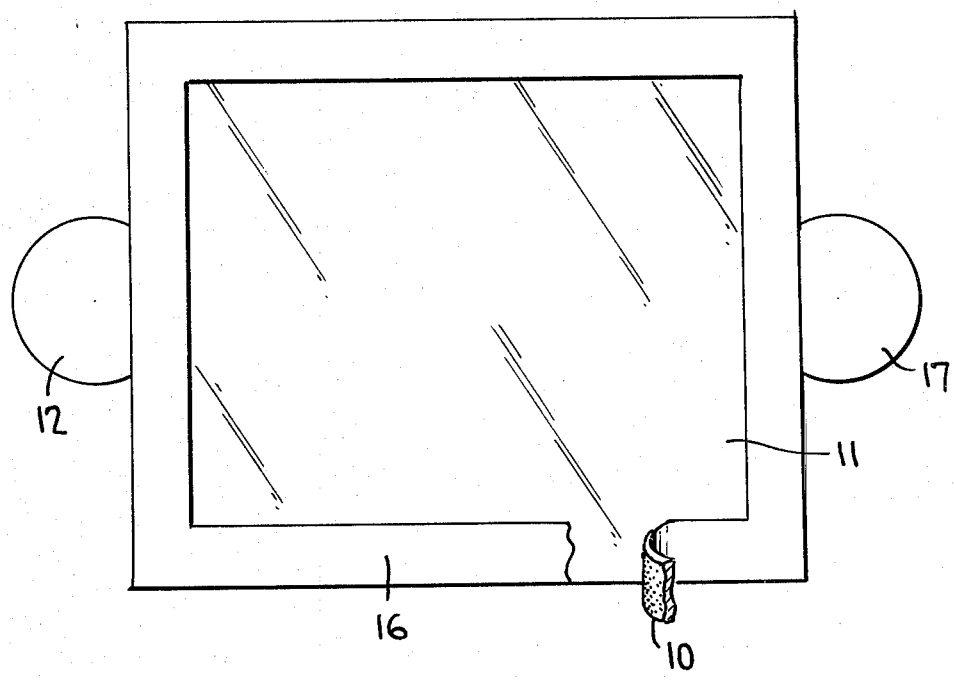
FIG. 5 is a plan view showing the top side of a covering comprising a second embodiment of the present invention.

Referring specifically to FIGS. 1-3 of the accompanying drawings, a covering for a topically applied applied salve or ointment includes a frame 10 of tape having adhesive applied to both sides, such tape being commercially available with peel-away or otherwise removable backing covering the adhesive surfaces. The tape material may be any type of medical foam, rayon, vinyl, etc. The frame is preferably rectangular with an open rectangular area within the confines of the frame. A sheet of moisture impervious material 11, cut to a rectangular shape having the same dimensions as the periphery of frame 10, is secured to the underside of frame 10 such that all of the adhesive material on that side of the frame is covered and such that the sheet 11 extends across the entire area surrounded by the frame. Sheet 11 may be transparent, opaque or translucent, although transparent material has the advantage of permitting the user to view the ointment and applicator during application of the covering. Suitable materials are polyethylene, vinyl, seran, polypropylene, etc. A small tab 12 extends from edge of sheet 11.

The top side of frame 10 is covered with a removable backing paper 13. A generally centrally located portion 14 of backing paper 13 is perforated for removable and has a configuration similar to the typical dose measuring applicator utilized for applying nitroglycerin to a patient's skin. Such an applicator 15 is disposed beneath tab 14 adjacent sheet 11 and is secured by means of a perforated tape 16 to the frame 10. Typically, dose measuring applicator 15 is a rectangular piece of parchment or other ointment impervious material which has a calibrated ointment receiving scale imprinted thereon. It is shown removed in FIG. 3.

In use, a nurse or other health care personnel lifts tab 14 away from backing 13 to expose the dose measuring applicator 15. A measured amount of ointment is squeezed from the ointment tube onto the calibrated scale. The nurse then holds tab 13 and, if desired, removes the applicator 15 from the unit and applies it directly to the sight of ointment administration on the patient's body. Alternatively, the applicator 15 may remain part of the assembly for purposes of application of the ointment to the body. In either case, still holding tab 12, the nurse removes backing 13 from the top side of frame 10, thereby exposing the adhesive material on the top side of the frame. The covering is then applied over the sight of application and the frame 10 pressed down on the skin to assure adherence thereto. The applied covering and applicator are illustrated in FIG. 4.

The preprepared covering described above eliminates the need for cutting plastic wrap and precut tape pieces to cover the sight of applied nitroglycerin for purposes of retaining moisture and facilitating absorption of the nitroglycerin into the circulatory system through the skin. The covering is inexpensive to fabricate, sufficiently so that the covering can be economically disposed of after a single use. Alternatively, to the extent that the adhesive coating on the top side of frame 10 retains, the covering can be used by the same patient for multiple applications of the nitroglycerin. If desired, the covering can be folded along dotted lines as shown, to facilitate application of ointment with applicator 15 intact.

Figure 6:
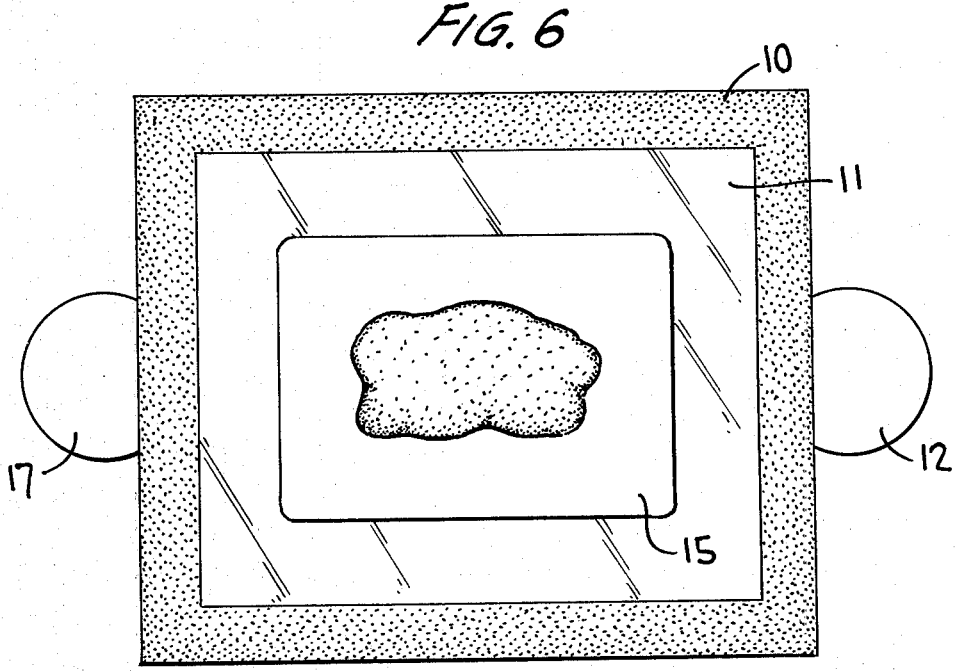
FIG. 6 is a plan view showing the bottom side of the covering of FIG. 5.

Another embodiment of the present invention is illustrated in FIGS. 5 and 6 wherein like elements are designated by the same reference numerals. Double sided tape frame 10 is covered entirely on one side with water impervious sheet material 11. The sheet material includes a pair of tabs 12 and 17 extending beyond opposite edges of the frame 10, which matches exactly the contour of frame 10. This embodiment eliminates the dose measuring after the dose measuring applicator is applied with the nitroglycerin to the desired sight on the patient's skin, backing 16 is peeled away from frame 10 and the exposed adhesive side of frame 10 is applied to the patient's skin over the region of ointment application. For this purpose, the dose measuring applicator may remain in place or be removed prior to application of the covering. Likewise, the dose measuring applicator may be left in place or removed prior to application of the covering of FIG. 1. In removing backing 16 and applying the exposed adhesive surface of tape 10 to the patient, the nurse or other health care personnel holds one or both of tabs 12 and 17 which have no adhesive backing and, in fact, are extensions of the moisture impervious material.

The dose measuring applicator is made of material which permits health care personnel to administer the ointment to a patient without ointment contact by the health care personnel. Specifically, the nurse or other personnel is able to measure the amount of ointment and prevent absorption of the ointment through his or her fingers during application.

The primary advantage of the embodiment of FIGS. 1-4 is the provision of the dose measuring applicator as an integral part of the cover arrangement so that ointment and sealing can be placed into position in one step instead of two.

The moisture retentive covering as described herein has a rectangular double-sided tape frame. The rectangular configuration is, of course, not a limiting feature of the invention; rather, it represents a configuration which is simple to fabricate and to use. Circular, elliptical, polygonal or any irregular configuration may be employed. Importantly, the area bounded by the frame, whatever its configuration, covered with a sheet of material which is light-weight, flexible and moisture impervious so that hydration will be enhanced in the covered area. As noted, the dose measuring applicator may be left under the covering or not, as desired by the user. The use of transparent material for the covering sheet has psychological advantages but is by no means necessary.

The removable backing employed by the frame member is conventionally available and widely used. Its primary characteristic is its non-porous surface which is removably secured to the adhesive material on the frame, but, upon removal, leaves the adhesive material substantially intact on the frame.

The present invention is not to be limited to the embodiments as herein described for numerous modifications can be made within the scope of the appended claims by a person skilled in the art without detracting from the spirit of the invention.

The embodiments of the invention in which an exclusive property or privilege is claimed are as follows:

1. A moisture-retentive covering for ointment applied to a portion of a patient's skin to promote hydration of the covered skin and maximizing percutaneous absorption of the ointment, said covering comprising:
    a flexible frame member defining a prescribed area slightly larger than said skin portion, said frame member having first and second surfaces with adhesive material on each surface;
    a sheet of moisture-impervious material secured to said first surface of said frame member by said adhesive material and entirely covering said first surface and said prescribed area;
    a removable backing secured to said second surface by said adhesive material and entirely covering said second surface, said removable backing being fabricated from a material which, upon removal from said second surface, leaves the adhesive material substantially intact on said second surface; and
    at least one tab extending from said sheet beyond said prescribed area defined by said frame for the purpose of permitting a user to grip the tab while removing said backing.

2. The moisture-retentive covering according to claim 1 wherein said tab is integral with said sheet.

3. The moisture-retentive covering according to claim 1 wherein said backing has the same configuration as said frame and covers only said second surface without covering said defined area.

4. The moisture-retentive covering according to claim 1 wherein said backing covers said second surface and said defined area.

5. The moisture-retentive covering according to claim 4 wherein said backing has a perforated area, said covering further comprising an ointment dose-measuring applicator secured to said frame member and disposed between said sheet and said backing in alignment with said perforated area, whereby detachment of said perforated portion exposes said ointment dose-measuring applicator.

6. The moisture-retentive covering according to claim 5 wherein said applicator is detachably secured to said frame member.

* * * * *